US010555958B2

(12) United States Patent
Reiche et al.

(10) Patent No.: US 10,555,958 B2
(45) Date of Patent: Feb. 11, 2020

(54) COMBINATION TREATMENT OF SGLT2 INHIBITORS AND DOPAMINE AGONISTS FOR PREVENTING METABOLIC DISORDERS IN EQUINE ANIMALS

(71) Applicant: Boehringer Ingelheim Vetmedica GmbH, Ingelheim am Rhein (DE)

(72) Inventors: Dania Birte Reiche, Bingen am Rhein (DE); Daniela Rahmel, Ingelheim am Rhein (DE)

(*) Notice: Subject to any disclaimer, the term of this patent is extended or adjusted under 35 U.S.C. 154(b) by 3 days.

(21) Appl. No.: 15/512,984

(22) PCT Filed: Sep. 22, 2015

(86) PCT No.: PCT/EP2015/071637
§ 371 (c)(1),
(2) Date: Mar. 21, 2017

(87) PCT Pub. No.: WO2016/046150
PCT Pub. Date: Mar. 31, 2016

(65) Prior Publication Data
US 2017/0239281 A1 Aug. 24, 2017

(30) Foreign Application Priority Data

Sep. 25, 2014 (EP) .................................... 14186479

(51) Int. Cl.
| A61K 31/437 | (2006.01) |
| A61K 31/351 | (2006.01) |
| A61P 3/10 | (2006.01) |
| A61P 3/00 | (2006.01) |
| A61K 31/70 | (2006.01) |
| A61K 31/4045 | (2006.01) |
| A61K 31/428 | (2006.01) |
| A61K 31/48 | (2006.01) |
| A61K 31/506 | (2006.01) |
| A61K 31/7034 | (2006.01) |
| A61K 31/7042 | (2006.01) |
| A61K 31/7048 | (2006.01) |
| A61K 31/7056 | (2006.01) |
| A61K 31/381 | (2006.01) |
| A61K 31/40 | (2006.01) |
| A61K 31/496 | (2006.01) |
| A61K 31/4985 | (2006.01) |
| A61K 31/55 | (2006.01) |

(52) U.S. Cl.
CPC ............ *A61K 31/70* (2013.01); *A61K 31/351* (2013.01); *A61K 31/381* (2013.01); *A61K 31/40* (2013.01); *A61K 31/4045* (2013.01); *A61K 31/428* (2013.01); *A61K 31/437* (2013.01); *A61K 31/48* (2013.01); *A61K 31/496* (2013.01); *A61K 31/4985* (2013.01); *A61K 31/506* (2013.01); *A61K 31/55* (2013.01); *A61K 31/7034* (2013.01); *A61K 31/7042* (2013.01); *A61K 31/7048* (2013.01); *A61K 31/7056* (2013.01); *A61P 3/00* (2018.01); *A61P 3/10* (2018.01)

(58) Field of Classification Search
CPC ........................... A61K 31/437; A61K 31/351
See application file for complete search history.

(56) References Cited

U.S. PATENT DOCUMENTS

| 7,371,732 B2 | 5/2008 | Eickelmann et al. |
| 7,375,090 B2 | 5/2008 | Himmelsbach et al. |
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,524,822 B2 | 4/2009 | Kraemer et al. |
| 7,579,449 B2 | 8/2009 | Eckhardt et al. |
| 7,589,193 B2 | 9/2009 | Washburn et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,378 B2 | 8/2010 | Himmelsbach et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,080,580 B2 | 12/2011 | Mascitti et al. |

(Continued)

FOREIGN PATENT DOCUMENTS

| CA | 2519584 A1 | 9/2005 |
| EP | 2048150 A1 | 4/2009 |

(Continued)

OTHER PUBLICATIONS

Definition of prevent, Oxford English Dictionary Online, http://dictionary.oed.com/, accessed online Mar. 27, 2010, especially definition 9a. at p. 2. (Year: 2010).*

(Continued)

*Primary Examiner* — Jonathan S Lau
(74) *Attorney, Agent, or Firm* — Judy Jarecki-Black

(57) ABSTRACT

The present invention relates to combination of one or more SGLT2 inhibitors or pharmaceutically acceptable forms and/or salts thereof and one or more dopamine receptor agonists or pharmaceutically acceptable forms and/or salts thereof, preferably in the treatment and/or prevention of a metabolic disorder of an equine animal, wherein more preferably the metabolic disorder is one or more disorders selected from Equine Metabolic Syndrome (EMS), Equine Pituitary Pars Intermedia Dysfunction (PPID), also known as equine Cushing's syndrome, laminitis, vascular dysfunction, hypertension, hepatic lipidosis, hyperadreeocorticism, glucose intolerance, insulin resistance, hyperinsulinaemia, hirsutism, hyperhidrosis. polyuria, polydipsia, chronic infections, abnormal fat distribution, muscle wasting, abnormal weight loss and/or loss of appetite.

18 Claims, No Drawings

(56) References Cited

U.S. PATENT DOCUMENTS

| | | | |
|---|---|---|---|
| 8,283,326 | B2 | 10/2012 | Eckhardt et al. |
| 8,283,454 | B2 | 10/2012 | Liou et al. |
| 8,507,450 | B2 | 8/2013 | Eckhardt et al. |
| 8,551,957 | B2 | 10/2013 | Dugi et al. |
| 8,987,323 | B2 | 3/2015 | Cai et al. |
| 9,145,434 | B2 | 9/2015 | Eckhardt et al. |
| 2003/0064935 | A1 | 4/2003 | Gougoutas |
| 2007/0259821 | A1 | 11/2007 | Eckhardt et al. |
| 2009/0143316 | A1 | 6/2009 | Imamura et al. |
| 2009/0285916 | A1* | 11/2009 | Haritou .......... A61K 31/13 424/730 |
| 2010/0167988 | A1 | 7/2010 | Gant et al. |
| 2010/0167989 | A1 | 7/2010 | Gant et al. |
| 2010/0249392 | A1 | 9/2010 | Eckhardt et al. |
| 2011/0046087 | A1* | 2/2011 | Eickelmann ....... A61K 31/7048 514/62 |
| 2012/0237593 | A1 | 9/2012 | Comiskey et al. |
| 2012/0277175 | A1 | 11/2012 | Neto et al. |
| 2014/0031540 | A1* | 1/2014 | Eckhardt ............ C07H 15/26 536/55 |
| 2014/0303096 | A1 | 10/2014 | Reiche et al. |
| 2015/0164856 | A1 | 6/2015 | Reiche et al. |
| 2015/0272977 | A1 | 10/2015 | Reiche et al. |
| 2016/0361289 | A1 | 12/2016 | Kley et al. |
| 2017/0056366 | A1 | 3/2017 | Weiler et al. |
| 2017/0071969 | A1 | 3/2017 | Reiche et al. |

FOREIGN PATENT DOCUMENTS

| | | |
|---|---|---|
| EP | 2368552 A1 | 9/2011 |
| WO | 0127128 A1 | 4/2001 |
| WO | 2002083066 A2 | 10/2002 |
| WO | 2004063209 A2 | 7/2004 |
| WO | 2007077457 A2 | 7/2007 |
| WO | 2007093610 A1 | 8/2007 |
| WO | 2007102999 A2 | 9/2007 |
| WO | 2007128749 A1 | 11/2007 |
| WO | 2007129053 A1 | 11/2007 |
| WO | 2008002824 A1 | 1/2008 |
| WO | 2008005240 A2 | 1/2008 |
| WO | 2008042688 A2 | 4/2008 |
| WO | 2008116179 A1 | 9/2008 |
| WO | 2009124755 A1 | 10/2009 |
| WO | 2009143020 A1 | 11/2009 |
| WO | 2010022313 A2 | 2/2010 |
| WO | 2010023594 A1 | 3/2010 |
| WO | 2010048358 A2 | 4/2010 |
| WO | 2010092125 A1 | 8/2010 |
| WO | 2010092123 A8 | 6/2011 |
| WO | 2011117295 A1 | 9/2011 |
| WO | 2011153712 | 12/2011 |
| WO | 2012062698 A1 | 5/2012 |
| WO | 2012140597 A1 | 10/2012 |
| WO | 2013040164 | 3/2013 |
| WO | 2014016381 A1 | 1/2014 |
| WO | 2014068007 A1 | 5/2014 |
| WO | 2014161836 A1 | 10/2014 |
| WO | 2015091313 A1 | 6/2015 |
| WO | 2015110402 A1 | 7/2015 |
| WO | 2015150299 A2 | 10/2015 |
| WO | 2016046150 A1 | 3/2016 |
| WO | 2017032799 A1 | 3/2017 |

OTHER PUBLICATIONS

McGowan, C.; Rand, J. ed., Clinical Endocrinology of Companion Animals, 2013, John Wiley & Sons, Inc., 1st ed, p. 100-114. (Year: 2013).*

Ashburn, William N., "Evolution of sodium glucose co-transporter 2 inhibitors as anti-diabetic agents." Expert Opinion on Therapeutic Patients, vol. 19, No. 11, 2009, pp. 1485-1499.

Ciobotaru, Emilia, "Diabetes Mellitus—Insights and Perspectives", Editor: Oluwafemi O. Oguntibeju, ISBN 978-953-51-0939-6, Jan. 2, 2013, Chapter 15, Spontaneous Diabetes Mellitus in Animals, pp. 271-296.

Yamamoto et al., "TS-071 is a novel, potent and selective renal sodium-glucose cotransporter 2 (SGLT2) inhibitor with anti-hyperglycaemic activity." British Journal of Pharmacology, vol. 164, No. 1, 2011, pp. 181-191.

Katsuno et al., "Sergliflozin, a Novel Selective Inhibitor of Low-Affinity Sodium Glucose Cotransporter (SGLT2), Validates the Critical Role of SGLT2 in Renal Glucose Reabsorption and Modulates Plasma Glucose Level." The Journal of Pharmacology and Experimental Therapeutics, vol. 320, No. 1, 2007, pp. 323-330.

Jeta et al., "Reduction of Renal Transport Maximum for Glucose by Inhibition of Na+—Glucose Cotransporter Suppresses Blood Glucose Elevation in Dogs." Biological and Pharmaceutical Bulletin, vol. 29, No. 1, 2006, pp. 114-118.

Grempler et al., "Empagliflozin, a novel selective sodium glucose cotransporter-2 (SGLT-2) inhibitor: characterisation and comparison with other SGLT-2 inhibitors." Diabetes, Obesity and Metabolism, vol. 14, 2012, pp. 83-90.

Sugimoto et al., "Novel Therapeutic Agents for the Treatment of Diabetes Sodium-Glucose Co-Transporter (SGLT) 2 Inhibitors." Cutting-Edge of Medicine, vol. 102, No. 6, 2013, pp. 1474-1483.

Diabetes, vol. 56, Suppl.1, 2007, pp. A144-A145.

De Laat et al., "Equine laminitis: Induced by 48 h hyperinsulinaemia in Standardbred horses". Equine Veterinary Journal, vol. 42, No. 2, 2010, pp. 129-135.

Durham et al., "Type 2 diabetes mellitus with pancreatic b cell dysfunction in 3 horses confirmed with minimal model analysis". Equine Veterinary Journal, vol. 41, No. 9, 2009, pp. 924-929.

Frank et al., "Equine Metabolic Syndrome", ACVIM Consensus Statement, Journal of Veterinary Internal Medicine, vol. 24, No. 3, 2010, pp. 467-475.

Gehlen et al., "Comparison of Insulin and Glucose Metabolism in Horses with Pituitary Pars Intermedia Dysfunction Treated Versus Not Treated with Pergolide". Journal of Equine Veterinary Science, vol. 34, 2014, pp. 508-513.

International Search Report and Written Opinion of PCT/EP2015/071637 dated Feb. 29, 2016.

Kakinuma et al., "(1S)-1,5-Anhydro-1-[5-(4-ethoxybenzyl)-2-methoxy-4-methylphenyl]-1-thio-d-glucitol (TS-071) is a Potent, Selective Sodium-Dependent Glucose Cotransporter 2 (SGLT2) Inhibitor for Type 2 Diabetes Treatment". Journal of Medicinal Chemistry, vol. 53, No. 8, 2010, pp. 3247-3261.

Sinha et al., "Pioglitazone—Do we really need it to manage type 2 diabetes?" Diabetes & Metabolic Syndrome: Clnical Research & Reviews, vol. 7, No. 1, 2013, pp. 52-55.

Tirmenstein et al., "Nonclinical Toxicology Assessments Support the Chronic Safety of Dapagliflozin, a First-in-Class Sodium-Glucose Cotransporter 2 Inhibitor". International Journal of Toxicology, vol. 32, No. 5, 2013, pp. 336-350.

Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes". Journal of Medicinal Chemistry, vol. 57, 2014, pp. 1236-1251.

Johnson et al., "Medical Implications of Obesity in Horses—Lessons for Human Obesity." Journal of Diabetes Science and Technology, vol. 3, No. 1, Jan. 2009, pp. 164-174.

French et al., "Pharmacokinetics and metabolic effects of triamcinolone anetonide and their possible relationships to glucocorticoid-induced laminitis in horses." Journal of Veterinary Pharmacology and Therapeutics, vol. 23, 2000, pp. 287-292.

Treiber et al., "Laminitis in Ponies is a Diabetic-like State" Experimental Biology, The FASEB Journal, Meeting Abstracts, vol. 21, No. 6, Abstract No. 737.23, Apr. 2007, p. A833. [Accessed at https://www.fasebj.org/doi/10.1096/fasebj.21.6.A833 on Apr. 17, 2018].

* cited by examiner

COMBINATION TREATMENT OF SGLT2 INHIBITORS AND DOPAMINE AGONISTS FOR PREVENTING METABOLIC DISORDERS IN EQUINE ANIMALS

FIELD OF THE INVENTION

The present invention relates to veterinary medicine, in particular to the combination treatment and/or prevention of metabolic disorders in equine animals.

BACKGROUND INFORMATION

Equine animals, e.g. horses, are affected by various metabolic disorders, including insulin resistance and hyperinsulinaemia. Insulin-related disorders are correlated or may be associated with a number of further equine disorders, conditions or syndromes, including impaired glucose tolerance, dyslipidaemia, dysadipokinaemia, obesity and/or regional adiposity, subclinical inflammation or systemic inflammation, in particular low grade systemic inflammation, which also comprises adipose tissue, Equine Metabolic Syndrome (EMS) and/or Equine Pituitary Pars Intermedia Dysfunction (PPID), also known as equine Cushing's syndrome. Both, EMS and PPID are characterized e.g. by laminitis, vascular dysfunction, hypertension, hepatic lipidosis, hyperadrenocorticism and/or atherosclerosis.

Such metabolic disorders in equine animals, for example, are only rarely associated with diabetes mellitus and hyperglycaemia as it is in humans or various other mammals.

In particular, insulin resistance in equine animals may be associated with EMS and/or PPID or may cause the development or progression of PPID. EMS and/or PPID may become manifest e.g. in laminitis. This devastating worldwide cause of mortality in horses is a multifactorial condition causing structural and mechanical changes in the supporting tissues within the hoof, resulting in acute and chronic pain, lameness, and potentially euthanasia. Equine laminae are highly metabolically active, and a complex microvascular bed is present. A significant body of evidence exists also for vascular dysfunction (endothelial cell dysfunction) during equine laminitis (Katz & Bailey, 2012). In vitro studies in equine digital vessels have shown insulin resistance-mediated endothelial and/or vascular dysfunction (Venugopal et al., 2011). A direct link between hyperinsulinaemia and laminitis has been documented in naturally-occurring forms of the disease (Treiber et al., 2006). However, the mechanism by which insulin resistance and/or hyperinsulinaemia cause EMS and/or PPID, in particular vascular dysfunction and/or laminitis in horses is poorly understood.

No satisfactory treatment is currently available for metabolic disorders such as insulin resistance, hyperinsulinaemia and associated disorders in equine animals, such as EMS and/or in case they are associated with or secondary to e.g. PPID, which become manifest e.g. by laminitis, vascular dysfunction, hypertension in equine animals. For instance, the use of Metformin is controversially discussed (Tinworth et al., 2012). Similarly, various treatment options are contemplated in equine PPID: dopamine receptor agonists (pergolide and bromocriptine), cortisol inhibitors (trilostane) and also serotonin antagonists (cyproheptidine) have been used (McGowan, 2005). But the effects of these treatments on insulin resistance and/or hyperinsulinaemia are controversial or seem to be hardly detectable e.g. with pergolide (Gehlen, 2014). In general high plasma insulin levels (unaffected by treatment) are associated with a poor outcome in horses suffering from equine PPID (McGowan, 2004).

In human medicine, insulin resistance, e.g. when manifest as diabetes mellitus type 2, is a well-recognised condition, and may lead in particular to hyperglycaemia (pathologically increased plasma glucose levels). Several oral antihyperglycaemic drugs are approved for human diabetes. These drugs act, e.g. by stimulating pancreatic insulin secretion in a glucose-independent or glucose-dependent manner (sulfonylurea/meglitinides or DPP IV inhibitors, respectively), by enhancing tissue sensitivity to insulin (biguanides, thiazolidinediones), or by slowing postprandial intestinal glucose absorption (alpha-glucosidase inhibitors).

Other antihyperglycaemic approaches have been contemplated for treating diabetes and high blood sugar, including inhibition of the renal sodium-dependent glucose cotransporter SGLT2. SGLT2 in the kidney regulates glucose levels by mediating the reabsorption of glucose back into the plasma following filtration of the blood. SGLT2 inhibition thus induces glucosuria and may reduce blood glucose levels.

SGLT2 inhibition has not previously been contemplated for use in equine animals, in particular in insulin-resistant equine animals. In equine animals, insulin-resistance, i.e. failure of tissues to respond appropriately to insulin, generally becomes manifest as hyperinsulinaemia. When insulin-resistant target tissues, e.g. skeletal muscle, have a reduced capacity for glucose uptake, the pancreas is stimulated to release more insulin, leading to hyperinsulinaemia. Insulin-resistant equine animals, e.g. horses, do not appear to have high blood glucose. For that reason, it would appear to be counter-intuitive to apply an approach that reduces blood glucose by transferring glucose out of the blood into the urine, even if this was previously known in a context of high blood glucose.

Further prior art is as follows:

U.S. Pat. No. 3,732,231 deals with D-6-methyl-8-cyanomethylergoline and a method of making the same, wherein the therein disclosed compounds constitute antifertility and lactation inhibiting agents.

U.S. Pat. No. 3,901,894 relates to 8-thiomethylergolines useful as prolactin inhibitors.

U.S. Pat. No. 3,920,664 is directed to D-2-halo-6-alkyl-8-substituted ergolines and related compounds that function as prolactin inhibitors.

U.S. Pat. No. 3,959,288 discloses 8-oxymethylergolines and a process of making the same, wherein the therein disclosed compounds constitute prolactin inhibitors.

EP 0 003 667 and U.S. Pat. No. 4,166,182 describe substituted ergolines, their preparation, compositions containing them and their use as pharmaceuticals, e.g. for the inhibition of prolactin secretion or the treatment of Parkinson's syndrome.

EP 0 026 671 and U.S. Pat. No. 4,246,265 deals with D-6-n-propylergoline derivatives compositions containing them and their use as pharmaceuticals, e.g. for lowering the prolactin levels in mammals or for treating symptoms of Parkinson's syndrome in humans.

EP 0 213 850 and U.S. Pat. No. 4,782,152 relates to a process for the decyanation of pergolide intermediate.

WO 96/40139 is directed to novel formulations for the transdermal delivery of pergolide.

WO 02/11727 discloses a formulation and a method of manufacturing stable pergolide mesylate.

WO 2007/129053 describes methods of diagnosis and treatment of equine laminitis and Cushing's syndrome.

The objective underlying the present invention is therefore to provide a medication for preventing and/or treating metabolic disorders in equine animals, which overcomes the problems of the prior art.

SUMMARY OF THE INVENTION

In one aspect, the objective of the present invention has surprisingly been solved by providing one or more SGLT2 inhibitors or pharmaceutically acceptable forms and/or salts thereof in combination with one or more dopamine receptor agonists or pharmaceutically acceptable forms and/or salts thereof for use as a medicament.

In another aspect, the objective of the present invention has surprisingly been solved by providing one or more SGLT2 inhibitors or pharmaceutically acceptable forms and/or salts thereof in combination with one or more dopamine receptor agonists or pharmaceutically acceptable forms and/or salts thereof for use in the treatment and/or prevention of a metabolic disorder of an equine animal, wherein preferably the metabolic disorder is one or more disorders selected from Equine Metabolic Syndrome (EMS), Equine Pituitary Pars intermedia Dysfunction (PPID), also known as equine Cushing's syndrome, laminitis, vascular dysfunction, hypertension, hepatic lipidosis, hyperadrenocorticism, glucose intolerance, insulin resistance, hyperinsulinaemia, hyperglycaemia, chronic infections, hirsutism, hyperhidrosis, polyuria, polydipsia, abnormal fat distribution, muscle wasting, abnormal weight loss and/or loss of appetite.

In yet another aspect, the objective of the present invention has surprisingly been solved by providing a pharmaceutical composition comprising one or more SGLT2 inhibitors or pharmaceutically acceptable forms and/or salts according to the present invention and one or more dopamine receptor agonists or pharmaceutically acceptable forms and/or salts according to the present invention for use as herein described.

The combination therapy according to the present invention advantageously leads to improved insulin sensitivity where monotherapy with one or more dopamine receptor agonist is insufficient, e.g. to normalize the insulin dysregulation in an equine animal, such as a horse, suffering from equine PPID. Preferably, such combination therapy is characterized through a simultaneous administration, sequential (in any order) administration, and/or chronologically staggered administration of the one or more SGLT2 inhibitors or pharmaceutically acceptable forms and/or salts according to the present invention and one or more dopamine receptor agonists or pharmaceutically acceptable forms and/or salts according to the present invention. Surprisingly, the combination therapy advantageously provides a countermeasure against frequently observed abnormal weight loss and/or loss of appetite in equine animals, particularly when suffering from PPID and being treated with one or more dopamine receptor agonists alone.

DETAILED DESCRIPTION OF THE INVENTION

The present inventors have surprisingly found that the inhibition of SGLT2 in combination with a dopamine receptor agonist is effective and safe in the treatment and/or prevention of metabolic disorders in equine animals. The present invention thus provides the use of an SGLT2 inhibitor or a pharmaceutically acceptable form thereof in the treatment and/or prevention of a metabolic disorder of an equine animal. Further aspects of the invention are defined below as well as in the claims.

According to the invention, the metabolic disorder may be insulin resistance, hyperinsulinaemia, and/or a clinical condition associated with insulin resistance and/or hyperinsulinaemia.

The metabolic disorder, or said clinical condition associated with insulin resistance and/or hyperinsulinaemia, may be one or more disorder selected from insulin resistance, hyperinsulinaemia, impaired glucose tolerance, dyslipidaemia, dysadipokinaemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction, Equine Metabolic Syndrome, chronic infections, hirsutism, hyperhidrosis, polyuria, polydipsia, abnormal fat distribution, muscle wasting, abnormal weight loss and/or loss of appetite.

According to the invention, the equine animal may be suffering from one or more of impaired glucose tolerance, dyslipidaemia, dysadipokinaemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction, Equine Metabolic Syndrome, chronic infections, hirsutism, hyperhidrosis, polyuria, polydipsia, abnormal fat distribution, muscle wasting, abnormal weight loss and/or loss of appetite.

According to the invention, impaired glucose tolerance, dyslipidaemia, dysadipokinaemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction, Equine Metabolic Syndrome, chronic infections, hirsutism, hyperhidrosis, polyuria, polydipsia, abnormal fat distribution, muscle wasting, abnormal weight loss and/or loss of appetite may be associated with hyperinsulinaemia and/or insulin resistance.

According to the invention, the metabolic disorder may be hyperinsulinaemia and/or insulin resistance, and said hyperinsulinaemia or insulin resistance may optionally be associated with one or more of impaired glucose tolerance, dyslipidaemia, dysadipokinaemia, subclinical inflammation, systemic inflammation, low grade systemic inflammation, chronic infections, polyuria, polydipsia, hirsutism, hyperhidrosis, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction and/or Equine Metabolic Syndrome.

The equine animal may, e.g., be a horse. The equine animal may, e.g., be a pony. The equine animal may be obese and/or exhibit regional adiposity and/or abnormal fat distribution. However, for instance as regards Pituitary Pars Intermedia Dysfunction, the equine animal may also be not obese and/or be present with muscle wasting and/or exhibit hyperglycaemia and/or abnormal body weight loss and/or loss of appetite. The equine animal might show normal appetite or reduced appetite.

According to the invention, polyuria and/or polydipsia may be associated with hyperinsulinaemia, insulin resistance, impaired glucose tolerance, dyslipidaemia, dysadipokinaemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction, Equine Metabolic Syndrome, chronic infections, hirsutism, hyperhidrosis, polyuria, polydipsia, abnormal fat distribution, muscle wasting, abnormal weight loss and/or loss of appetite.

The pharmaceutically acceptable form of the SGLT2 inhibitor may be a crystalline complex between the SGLT2 inhibitor and one or more amino acids, e.g. proline.

According to the invention, the SGLT2 inhibitor or pharmaceutically acceptable forms and/or salts thereof may be provided, e.g., for oral or parenteral administration, preferably for oral administration.

The SGLT2 inhibitor or pharmaceutically acceptable forms and/or salts thereof may be administered in dosages of 0.01 to 3.0 mg/kg body weight per day, preferably from 0.02 to 1.0 mg/kg body weight per day, more preferably from 0.03 to 0.4 mg/kg body weight per day. Thus, the SGLT2 inhibitor or pharmaceutically acceptable form thereof may be prepared for the administration of 0.01 to 3.0 mg/kg body weight per day, preferably from 0.02 to 1.0 mg/kg body weight per day, more preferably from 0.03 to 0.4 mg/kg body weight per day.

The total daily dose of the one or more SGLT2 inhibitor or pharmaceutically acceptable forms and/or salts thereof per equine animal is preferably from 10 mg to 500 mg.

The SGLT2 inhibitor or pharmaceutically acceptable forms and/or salts thereof is preferably administered only once per day.

The pharmaceutically acceptable forms and/or salts of the one or more dopamine receptor agonists may be the mesylate salt.

According to the invention, the one or more dopamine receptor agonists or pharmaceutically acceptable forms and/or salts thereof may be provided, e.g., for oral or parenteral administration, preferably for oral administration.

The one or more dopamine receptor agonists or pharmaceutically acceptable forms and/or salts thereof may be administered in dosages of 0.01 to 100 µg/kg bodyweight per day, preferably from 0.1 to 100 µg/kg bodyweight per day, more preferably from 0.1 to 10 µg/kg bodyweight per day. Further preferred dosages are from 0.6 to 10 µg/kg bodyweight per day, from 1.3 to 2.5 µg/kg bodyweight per day, from 1.7 to 2.5 µg/kg bodyweight per day, from 1.8 to 2.5 µg/kg bodyweight per day, or from 2.0 to 2.4 µg/kg bodyweight per day. Thus, the one or more dopamine receptor agonists or pharmaceutically acceptable forms and/or salts thereof may be prepared for the administration of 0.01 to 100 µg/kg bodyweight per day, preferably from 0.1 to 100 µg/kg bodyweight per day, more preferably from 0.1 to 10 µg/kg bodyweight per day. Further preferred are from 0.6 to 10 µg/kg bodyweight per day, from 1.3 to 2.5 µg/kg bodyweight per day, from 1.7 to 2.5 µg/kg bodyweight per day, from 1.8 to 2.5 µg/kg bodyweight per day, or from 2.0 to 2.4 µg/kg bodyweight per day. The total daily dose of the one or more dopamine receptor agonists or pharmaceutically acceptable forms and/or salts thereof per equine animal is preferably from 0.05 mg to 50 mg.

The dopamine receptor agonist or pharmaceutically acceptable form thereof is preferably administered only once per day.

In a preferred embodiment of the invention a combination therapy of one or more SGLT2 inhibitors and one or more dopamine receptor agonists is employed. Such a combination advantageously leads to improved insulin sensitivity where monotherapy with one or more dopamine receptor agonist is insufficient, e.g. to normalize the insulin dysregulation in an equine animal, such as a horse, suffering from equine PPID. Preferably, such combination is characterized through a simultaneous administration, sequential (in any order) administration, and/or chronologically staggered administration.

According to the present invention, any known SGLT2 inhibitor or pharmaceutically acceptable forms and/or salts thereof may be used. In preferred embodiments, the SGLT2 inhibitor is a glucopyranosyl-substituted benzene derivative. A number of SGLT2 inhibitors which may be used according to the invention are described in detail herein below.

According to the present invention, any known dopamine receptor agonist or pharmaceutically acceptable forms and/or salts thereof may be used. In preferred embodiments, the dopamine receptor agonist is an ergoline derivative. A number of dopamine receptor agonists which may be used according to the invention are described in detail herein below.

The present invention also provides a pharmaceutical composition comprising one or more SGLT2 inhibitor or pharmaceutically acceptable forms and/or salts thereof as described herein and one or more dopamine receptor agonists or pharmaceutically acceptable forms and/or salts thereof as described herein for use according to the invention as disclosed herein.

In the examples provided herein, therapeutic and prophylactic benefits resulting from inhibition of SGLT2 in combination with a dopamine receptor agonist according to the present invention are demonstrated experimentally. Experimental data disclosed herein are intended to illustrate the invention, but not to have any limiting effect upon the scope of protection.

In particular, the present inventors have surprisingly found that the use of one or more SGLT2 inhibitors in combination with one or more dopamine receptor agonists according to the present invention advantageously leads to a reduction in insulin resistance in treated, insulin resistant equine animals. That is, equivalently, the use of one or more SGLT2 inhibitors in combination with one or more dopamine receptor agonists according to the present invention advantageously leads to increased insulin sensitivity in treated, insulin resistant equine animals.

The use of one or more SGLT2 inhibitors in combination with one or more dopamine receptor agonists according to the present invention advantageously leads to reduced plasma insulin levels, i.e. allows effective treatment of hyperinsulinaemia. Thus, the use of one or more SGLT2 inhibitor in combination with one or more dopamine receptor agonists according to the present invention advantageously leads to reduced baseline plasma insulin levels, and/or a reduced insulin excursion due to a glycaemic challenge, e.g. as measured during an intravenous glucose tolerance test (ivGTT), an oral sugar test (OST) or after any other form of glucose intake, e.g. after a meal (postprandial insulin excursion).

The use of one or more SGLT2 inhibitors in combination with one or more dopamine receptor agonists according to the present invention advantageously leads to a reduction in hyperinsulinaemia and surrogate markers of insulin resistance in treated, insulin resistant equine animals.

The glucose excursion after a challenge with insulin (e.g. in an intravenous insulin tolerance test (ivITT)), or after a challenge with glucose (e.g. as measured during an intravenous glucose tolerance test (ivGTT), an oral sugar test (OST) or after any other form of glucose intake, e.g. after a meal (postprandial glucose excursion)), or as measured in a combined glucose-insulin tolerance test (CGIT), of an equine animal treated in accordance with the invention is, advantageously, also improved. That is, after a challenge with insulin, the decrease in glucose levels is greater and/or more rapid; or after a challenge with glucose, the glycaemic peak of the glucose excursion is lowered and/or the duration of the glucose excursion is reduced.

The use of one or more SGLT2 inhibitors in combination with one or more dopamine receptor agonists according to the present invention thus generally leads to improved (i.e. increased) glucose tolerance, i.e., equivalently, reduces glucose intolerance.

The use of one or more SGLT2 inhibitors in combination with one or more dopamine receptor agonists according to the present invention thus generally leads to reduced ACTH levels and subsequently reduced cortisol levels, i.e. normalizes hyperadrenocorticism. Thus, the combined use of one or more SGLT2 inhibitors and one or more dopamine receptor agonists allows the improvement of clinical signs associated with the metabolic disorder, e.g. laminitis, vascular dysfunction, hypertension, hepatic lipidosis, chronic infections, hyperglycaemia, glucose intolerance, insulin resistance, hyperinsulinaemia, hirsutism, hyperhidrosis, polyuria, polydipsia, abnormal fat distribution, muscle wasting, abnormal weight loss and/or loss of appetite.

The use of one or more SGLT2 inhibitors in combination with one or more dopamine receptor agonists according to the present invention advantageously also leads to a reduction in plasma levels of non-esterified fatty acids, or an improved elimination of non-esterified fatty acids (NEFAs) from the bloodstream e.g. after a challenge with insulin (e.g., as measured during an intravenous insulin tolerance test (ivITT)), or after a challenge with glucose (e.g. as measured during an intravenous glucose tolerance test (ivGTT), an oral sugar test (OST) or after any other form of glucose intake, e.g. after a meal, that initiates a blood insulin excursion, or as measured in a combined glucose-insulin tolerance test (CGIT)).

The use of one or more SGLT2 inhibitors in combination with one or more dopamine receptor agonists according to the present invention advantageously also leads to a reduction in body fat and improved adipokine profile, e.g. reduced blood leptin levels. The invention is also associated with anti-obesity effects, and/or lead to a decrease in body mass in an equine animal. In one aspect, the invention thus allows obesity and/or obesity-related metabolic disorders to be managed in an equine animal.

The use of one or more SGLT2 inhibitors in combination with one or more dopamine receptor agonists according to the present invention generally reduces dyslipidaemia, dysadipokinaemia, obesity and/or regional adiposity. Thus, the combined use of one or more SGLT2 inhibitors and one or more dopamine receptor agonists allows the treatment and/or prevention of dyslipidaemia, dysadipokinaemia, obesity and/or regional adiposity, in particular when associated with insulin resistance and/or hyperinsulinaemia in equine animal.

Advantageously, the use of one or more SGLT2 inhibitors in combination with one or more dopamine receptor agonists according to the present invention does not cause hypoglycaemia.

The effects of the uses according to the present invention (i.e. the above-mentioned beneficial effects upon insulin resistance/sensitivity, insulin excursion, second phase insulin secretion, glucose tolerance, cortisol levels, elimination of non-esterified fatty acids, body fat, and/or blood leptin levels) are also advantageous in that they allow for the prevention of complications of insulin resistance and/or hyperinsulinaemia, and the treatment, prevention and/or control of further metabolic disorders, symptoms and/or clinical conditions that are associated with insulin resistance and/or hyperinsulinaemia in equine animals. They thus allow the possibility of preventing and/or delaying the onset of such complications, further metabolic disorders, symptoms and/or clinical conditions in equine animals.

The use of one or more SGLT2 inhibitors in combination with one or more dopamine receptor agonists according to the present invention also provides for treatment and/or prevention of laminitis, i.e. leads to reduction of lameness and/or time to recovery from a laminitis episode.

The use of one or more SGLT2 inhibitors in combination with one or more dopamine receptor agonists according to the present invention provides for treatment and/or prevention of vascular dysfunction, i.e. improvement of altered digital perfusion and/or improved vascular response to contractile or dilatatory stimuli.

The use of one or more SGLT2 inhibitors in combination with one or more dopamine receptor agonists according to the present invention also provides for treatment and/or prevention of Equine Metabolic Syndrome (EMS).

The use of one or more SGLT2 inhibitors in combination with one or more dopamine receptor agonists according to the present invention also provides for treatment of clinical symptoms associated with PPID, i.e. prevention of the development and/or progression of clinical symptoms associated with PPID in an equine animal.

The use of one or more SGLT2 inhibitors in combination with one or more dopamine receptor agonists according to the present invention may prevent the development and/or recurrence of laminitis in an equine animal suffering from EMS and/or PPID.

The use of one or more SGLT2 inhibitors in combination with one or more dopamine receptor agonists according to the present invention may prevent the development and/or recurrence of vascular dysfunction in an equine animal suffering from EMS and/or PPID.

The use of one or more SGLT2 inhibitors in combination with one or more dopamine receptor agonists according to the present invention may prevent the development and/or recurrence of hypertension in an equine animal suffering from EMS and/or PPID.

The use of one or more SGLT2 inhibitors in combination with one or more dopamine receptor agonists according to the present invention may prevent the development and/or recurrence of hepatic lipidosis in an equine animal suffering from EMS and/or PPID.

The use of one or more SGLT2 inhibitors in combination with one or more dopamine receptor agonists according to the present invention may prevent the development and/or recurrence of regional obesitas and/or abnormal fat distribution in an equine animal suffering from EMS and/or PPID.

The use of one or more SGLT2 inhibitors in combination with one or more dopamine receptor agonists according to the present invention may prevent the development and/or recurrence of glucose intolerance in an equine animal suffering from EMS and/or PPID.

The use of one or more SGLT2 inhibitors in combination with one or more dopamine receptor agonists according to the present invention may prevent the development and/or recurrence of insulin resistance and/or hyperinsulinaemia in an equine animal suffering from EMS and/or PPID.

The use of one or more SGLT2 inhibitors in combination with one or more dopamine receptor agonists according to the present invention may prevent the development and/or recurrence of hirsutism in an equine animal suffering from EMS and/or PPID.

The use of one or more SGLT2 inhibitors in combination with one or more dopamine receptor agonists according to the present invention may prevent the development and/or recurrence of hyperhidrosis in an equine animal suffering from EMS and/or PPID.

The use of one or more SGLT2 inhibitors in combination with one or more dopamine receptor agonists according to the present invention may prevent the development and/or recurrence of polyuria in an equine animal suffering from EMS and/or PPID.

The use of one or more SGLT2 inhibitors in combination with one or more dopamine receptor agonists according to the present invention may prevent the development and/or recurrence of polydipsia in an equine animal suffering from EMS and/or PPID.

The use of one or more SGLT2 inhibitors in combination with one or more dopamine receptor agonists according to the present invention may prevent the development and/or recurrence of muscle wasting in an equine animal suffering from EMS and/or PPID.

The use of one or more SGLT2 inhibitors in combination with one or more dopamine receptor agonists according to the present invention may prevent the development and/or recurrence of weight loss in an equine animal suffering from EMS and/or PPID.

The use of one or more SGLT2 inhibitors in combination with one or more dopamine receptor agonists according to the present invention may prevent the development and/or recurrence of loss of appetite in an equine animal suffering from EMS and/or PPID.

The effects of using one or more SGLT2 inhibitors in combination with one or more dopamine receptor agonists according to the present invention (e.g. the above-mentioned beneficial effects upon insulin resistance/sensitivity, plasma insulin levels, insulin excursion, glucose excursion, glucose tolerance, elimination of non-esterified fatty acids, body fat, and/or blood leptin levels) may be relative to the same or a comparable equine animal prior to administration of one or more SGLT2 inhibitors in combination with one or more dopamine receptor agonists according to the present invention, and/or relative to a comparable equine animal that has not received said treatment (e.g. a placebo group) and/or equine animals that received the respective monotherapies with one or more SGLT2 inhibitor or one or more dopamine receptor agonists. In either case, when a comparison is made, the comparison may be made after a certain treatment period, e.g., 1 week, 2 weeks, 3 weeks, 4 weeks, 1 month, 2 months, 3 months, 4 months, 5 months, 6 months, 7 months, 8 months, 9 months, 10 months, 11 months or 12 months. Preferably the treatment period is 3 months or more months, e.g. between 3 months and 12 months.

The use of one or more SGLT2 inhibitors in combination with one or more dopamine receptor agonists according to the present invention may be life-long.

Generally, the use of one or more SGLT2 inhibitors in combination with one or more dopamine receptor agonist according to the present invention may thus attenuate, delay or prevent the progression of a metabolic disorder, e.g. the metabolic disorders disclosed herein, or may delay or prevent the onset of metabolic disorders and their complications in equine animals.

The invention also provides methods of treating and/or preventing metabolic disorders in equine animals, comprising administering an effective dose of one or more SGLT2 inhibitors in combination with an effective dose of one or more dopamine receptor agonist as described herein to an equine animal in need of such treatment and/or prevention.

Definitions

All values and concentrations presented herein are subject to inherent variations acceptable in biological science within an error of ±10%. The term "about" also refers to this acceptable variation.

Treatment effects disclosed herein (such as an improvement, reduction or delayed onset of a disorder, disease or condition, or the improvement, reduction, increase or delay of any effect, index, marker level or other parameter relating to a disorder, disease or condition) may be observed with a statistical significance of $p<0.05$, preferably $<0.01$.

When reference is made herein to a deviation (e.g. an increase, elevation, excess, prolongation, raise, reduction, decrease, improvement, delay, abnormal levels, or any other change, alteration or deviation with respect to a reference), the deviation may be, e.g., by 5% or more, particularly 10% or more, more particularly 15% or more, more particularly 20% or more, more particularly 30% or more, more particularly 40% or more, or more particularly 50% or more, with respect to the relevant reference value, unless otherwise stated. Typically, the deviation will be by at least 10%, i.e. 10% or more. The deviation may also be by 20%. The deviation may also be by 30%. The deviation may also be by 40%. The relevant reference value may be generated from a group of reference animals which are treated with placebo instead of a combination of an SGLT2 inhibitor and a dopamine receptor agonist.

Herein, an excursion, e.g. an insulin excursions or glucose excursion, designates a change in concentration or level in blood over time. The magnitude of excursions, e.g. insulin excursions or glucose excursions may be expressed as area-under-curve (AUC) values.

Herein, the terms "active substance" or "active ingredient" encompass one or more SGLT2 inhibitors or any pharmaceutically acceptable forms and/or salts thereof (e.g. a prodrug or a crystalline form) or one or more dopamine receptor agonists or any pharmaceutically acceptable forms and/or salts thereof (e.g. mesylate salt); or a combination of both for use according to the invention. In the case of a combination, the terms "active ingredient" or "active substance" may also include the respectively other active pharmaceutical ingredients (APIs).

Herein, the expression "associated with", in particular encompasses the expression "caused by".

Herein, ivGTT refers to an intravenous glucose tolerance test. In an ivGTT, 0.2 g dextrose per kg body mass may typically be employed.

Herein, ivITT refers to an intravenous insulin tolerance test. In an ivITT, 0.03 IU insulin per kg body mass may typically be employed.

Herein, CGIT refers to a combined glucose-insulin tolerance test. In a CGIT, 0.15 mg glucose per kg body mass and 0.1 IU insulin per kg body mass may typically be employed.

Herein, OST refers to an oral sugar test. In an OST, 0.15 mL corn syrup per kg body mass may typically be employed.

The gold standard for the diagnosis of PPID is the resting ACTH concentration test, an overnight dexamethasone suppression test, and/or thyrotropin releasing hormone (TRH) stimulation test (Frank et al, 2011).

SGLT2 Inhibitors

SGLT2 inhibitors for use according to the invention include, but are not limited to, glucopyranosyl-substituted benzene derivatives, for example as described in WO 01/27128, WO 03/099836, WO 2005/092877, WO 2006/034489, WO 2006/064033, WO 2006/117359, WO 2006/117360, WO 2007/025943, WO 2007/028814, WO 2007/

031548, WO 2007/093610, WO 2007/128749, WO 2008/049923, WO 2008/055870, WO 2008/055940, WO 2009/022020, WO 2009/022008 or WO 2014/016381.

Moreover, the one or more SGLT2 inhibitors for use according to the invention may be selected from the group consisting of the following compounds or pharmaceutically acceptable forms thereof:

(1) a glucopyranosyl-substituted benzene derivative of the formula (1)

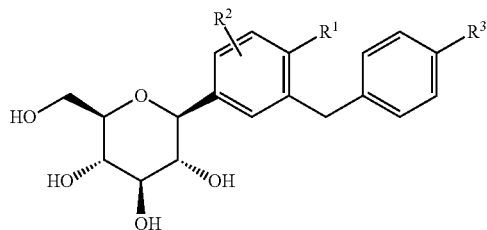

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methylsulfonyl, ethylsulfinyl, ethylsulfonyl, trimethylsilyl, (R)-tetrahydrofuran-3-yloxy or (S)-tetrahydrofuran-3-yloxy or cyano;

wherein R3 is preferably selected from cyclopropyl, ethyl, ethinyl, ethoxy, (R)-tetrahydrofuran-3-yloxy or (S)-tetrahydrofuran-3-yloxy; and most preferably R3 is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) 1-cyano-2-(4-cyclopropyl-benzyl)-4-(β-D-glucopyranos-1-yl)-benzene, represented by formula (2):

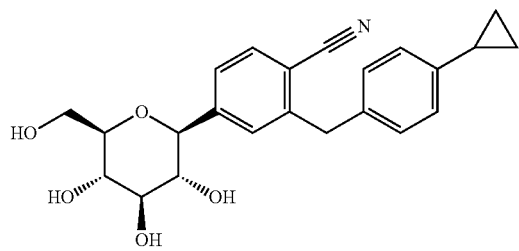 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

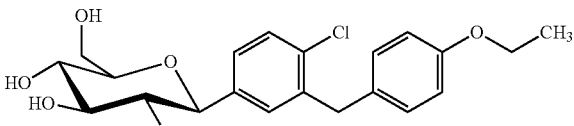

(4) Canagliflozin, represented by formula (4):

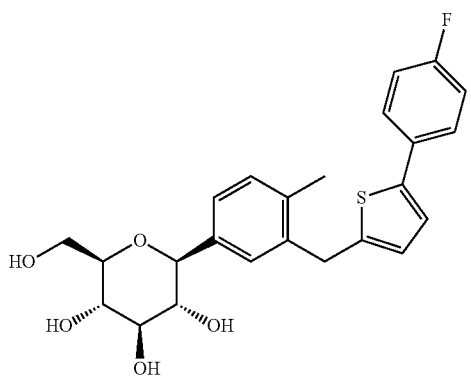 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

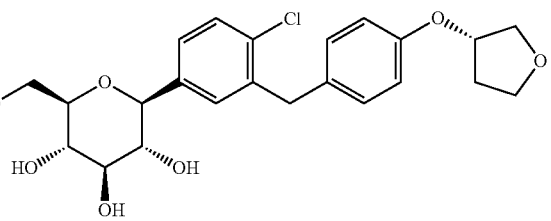

(6) Luseogliflozin, represented by formula (6):

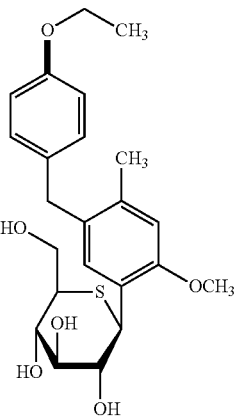

(7) Tofogliflozin, represented by formula (7):

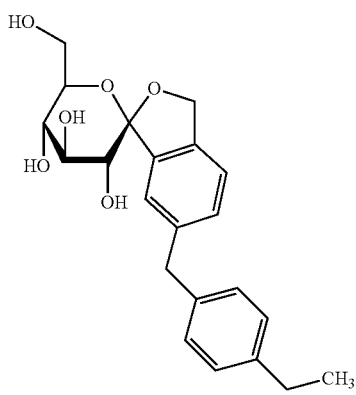

(8) Ipragliflozin, represented by formula (8):

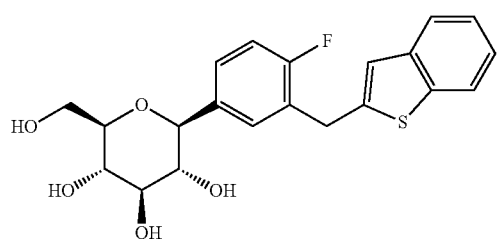 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

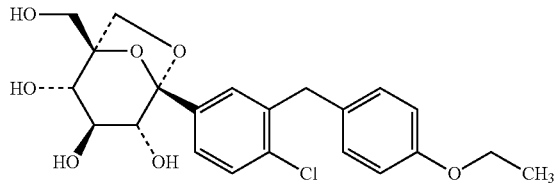 [SMILES: CCOc1ccc(Cc2cc([C@]34OC[C@](CO)(O3)[C@@H](O)[C@H](O)[C@H]4O)ccc2Cl)cc1]

(10) Atigliflozin, represented by formula (10):

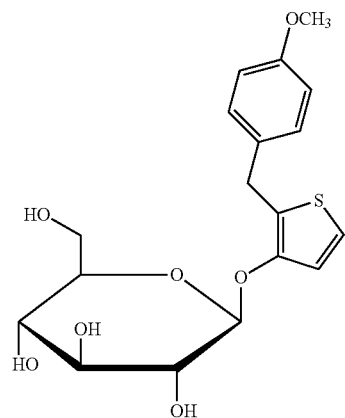

(11) Remogliflozin, represented by formula (11):

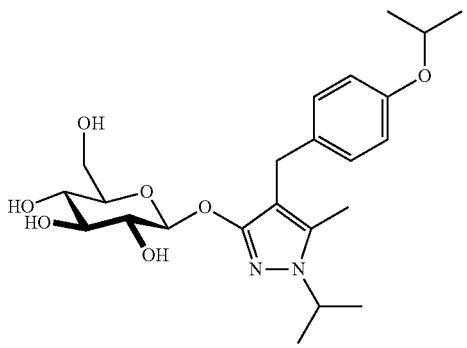

(12) a thiophene derivative of the formula (12)

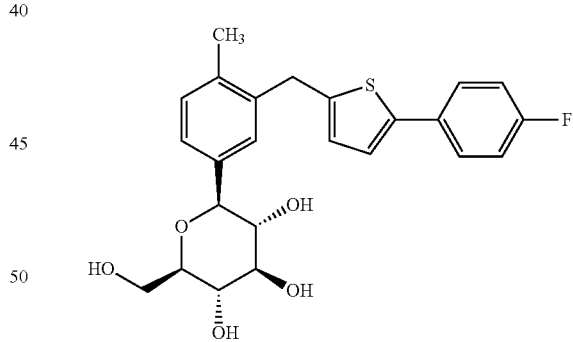

wherein R denotes methoxy or trifluoromethoxy;

(13) 1-(β-D-glucopyranosyl)-4-methyl-3-[5-(4-fluorophenyl)-2-thienytmethyl]benzene as described in WO2005/012326, represented by formula (13);

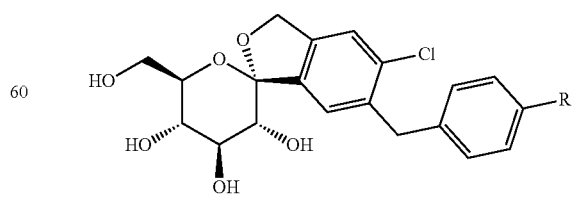

(14) a spiroketal derivative of the formula (14):

wherein R denotes methoxy, trifluoromethoxy, ethoxy, ethyl, isopropyl or tert. butyl;

(15) a pyrazole-O-glucoside derivative of the formula (15)

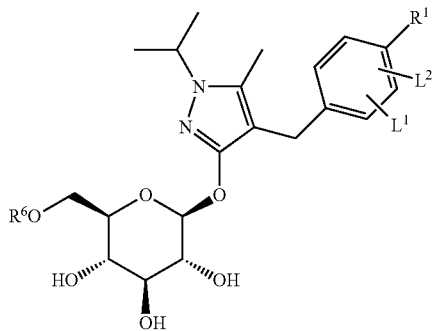

wherein
R¹ denotes $C_{1-3}$-alkoxy,
L¹, L² independently of each other denote H or F,
R⁶ denotes H, ($C_{1-3}$-alkyl)carbonyl, ($C_{1-6}$-alkyl)oxycarbonyl, phenyloxycarbonyl, benzyloxycarbonyl or benzylcarbonyl;
(16) a compound of the formula (16):

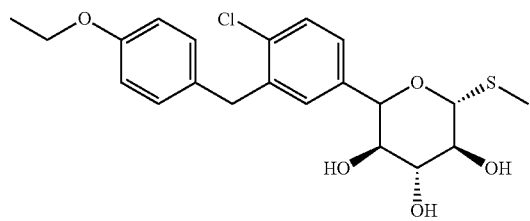 [SMILES: CCOc1ccc(Cc2cc(C3O[C@H](SC)[C@@H](O)[C@H](O)[C@H]3O)ccc2Cl)cc1]

(17) and Sergliflozin, represented by formula (17):

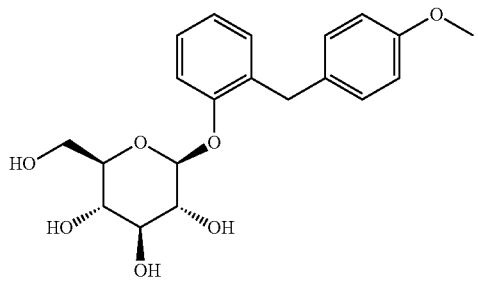 [SMILES: COc1ccc(Cc2ccccc2O[C@@H]2O[C@H](CO)[C@@H](O)[C@H](O)[C@H]2O)cc1]

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO 2005/012326 and WO 2009/035969 for example. Preferred hydrates, solvates and crystalline forms are described in the patent application WO 2008/069327 for example.

The term "empagliflozin" as employed herein refers to empagliflozin of the above structure as well as pharmaceutically acceptable forms thereof, including hydrates and solvates thereof, and crystalline forms thereof. The compound and methods of its synthesis are described in WO 2005/092877, WO 2006/120208 and WO 2011/039108 for example. A preferred crystalline form is described in the patent applications WO 2006/117359 and WO 2011/039107 for example.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO 2004/007517 for example.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO 2004/080990, WO 2005/012326 and WO 2007/114475 for example.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO 2007/140191 and WO 2008/013280 for example.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO 2010/023594.

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP 1 213 296 and EP 1 354 888 for example.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP 1 344 780 and EP 1 489 089 for example.

The compound of formula (16) above and its manufacture are described for example in WO 2008/042688 or WO 2009/014970.

Preferred SGLT2 inhibitors are glucopyranosyl-substituted benzene derivatives. Optionally, one or more hydroxyl groups of the glucopyranosyl group in such an SGLT2 inhibitor may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

More preferred are glucopyranosyl-substituted benzonitrile derivatives of formula (1) as disclosed herein above. Yet more preferred are glucopyranosyl-substituted benzonitrile derivatives of formula (18):

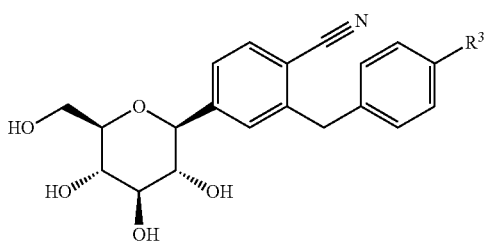

wherein

R3 denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methylsulfonyl, ethylsulfinyl, ethylsulfonyl, trimethylsilyl, (R)-tetrahydrofuran-3-yloxy or (S)-tetrahydrofuran-3-yloxy or cyano (wherein R3 is preferably selected from cyclopropyl, ethyl, ethinyl, ethoxy, (R)-tetrahydrofuran-3-yloxy or (S)-tetrahydrofuran-3-yloxy; and R3 most preferably is cyclopropyl), or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl.

Preferably, such SGLT2 inhibitor is 1-cyano-2-(4-cyclopropyl-benzyl)-4-(β-D-glucopyranos-1-yl)-benzene as shown in formula (2) (also referred to herein as "compound A"). Optionally, one or more hydroxyl groups of the β-D-glucopyranosyl group of compound A may be acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl.

Thus, in preferred embodiments, the one or more SGLT2 inhibitors according to the present invention is a glucopyranosyl-substituted benzene derivative SGLT2 inhibitor, preferably a SGLT2 inhibitor of formula (1), more preferably of formula (18) or yet more preferably of formula (2) (i.e. compound A), in each case as defined herein above.

Dopamine Receptor Agonists

The one or more dopamine receptor agonists for use according to the invention include, but are not limited to, ergoline derivatives and/or are preferably selected from the group consisting of:

(1) an ergoline derivative of the formula (19)

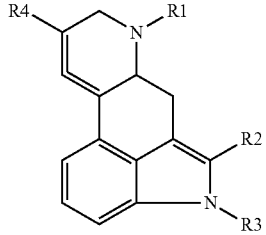

wherein independently from each other
R1 denotes C1-C6-alkyl, preferably methyl, ethyl, n-propyl or allyl;

R2 denotes hydrogen or halogen, preferably hydrogen, chloro or bromo;

R3 denotes hydrogen or C1-C6-alkyl, preferably hydrogen or methyl;

R4 denotes C1-C6-alkyl, wherein one or more —CH$_2$— groups can be replaced by O, S, SO or SO$_2$, preferably —CH$_2$—S—CH$_3$;

the dotted lines represent the optional presence of a double bond;

(2) (8β)-8-[(methylthio)methyl]-6-propylergoline (pergolide; and herein also referred to as "compound B"), represented by formula (20):

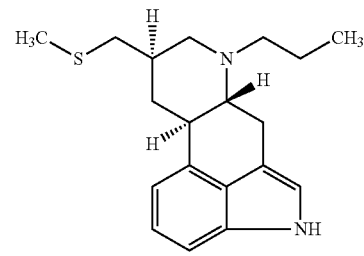 [SMILES: CCCN1C[C@H](CSC)C[C@@H]2c3cccc4[nH]cc(c34)C[C@H]21]

(3) Bromocriptine, represented by formula (21):

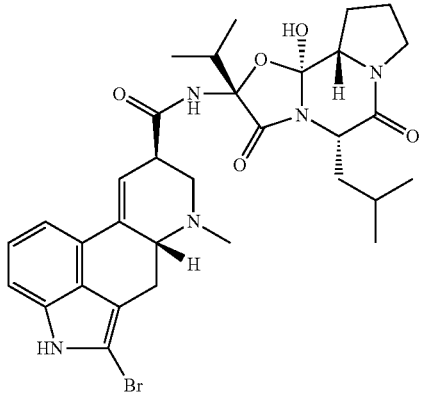

(4) Lisuride, represented by formula (22):

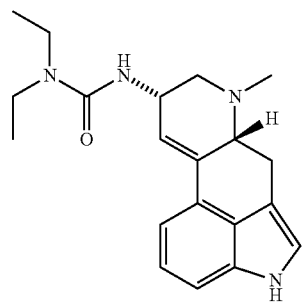 [SMILES: CCN(CC)C(=O)N[C@H]1C=C2c3cccc4[nH]cc(c34)C[C@H]2N(C)C1]

(5) Cabergoline, represented by formula (23):

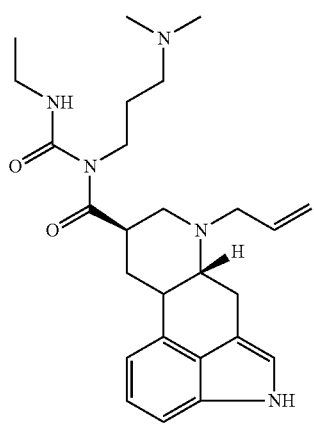 [SMILES: C=CCN1C[C@H](C(=O)N(CCCN(C)C)C(=O)NCC)CC2c3cccc4[nH]cc(c34)C[C@H]21]

(6) Alpha-Dihydroergocryptine, represented by formula (24):

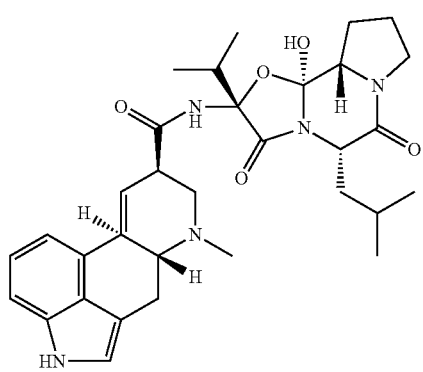

(7) Terguride, represented by formula (25)

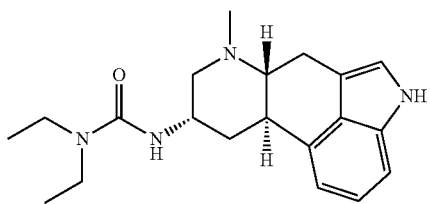 [SMILES: CCN(CC)C(=O)N[C@H]1C[C@@H]2c3cccc4[nH]cc(c34)C[C@H]2N(C)C1]

(8) Ropinirole, represented by formula (26):

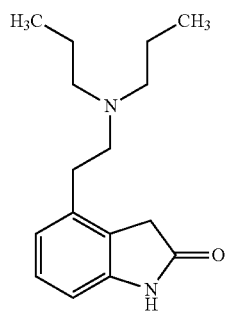

(9) (S)-2-Amino-6-(propylamino)-4,5,6,7-tetrahydrobenzothiazol (pramipexole), represented by formula (27):

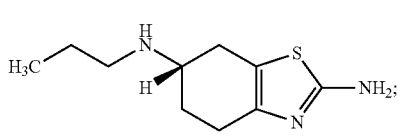

(10) Taipexole, represented by formula (28):

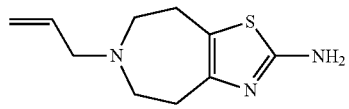

(11) Piroheptine, represented by formula (29):

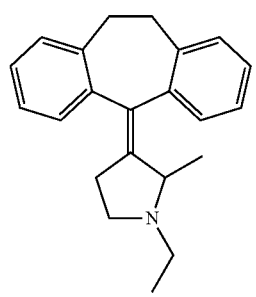 [SMILES: CCN1CCC(=C2c3ccccc3CCc3ccccc32)C1C]

(12) Quinagolide, represented by formula (30):

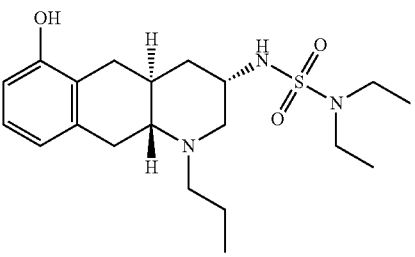 [SMILES: CCCN1C[C@@H](NS(=O)(=O)N(CC)CC)C[C@@H]2Cc3c(O)cccc3C[C@H]21]

(13) Piribedil, represented by formula (31):

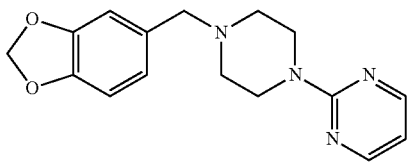 [SMILES: c1cnc(N2CCN(Cc3ccc4c(c3)OCO4)CC2)nc1]

(14) Rotigotine (N-0923), represented by formula (32):

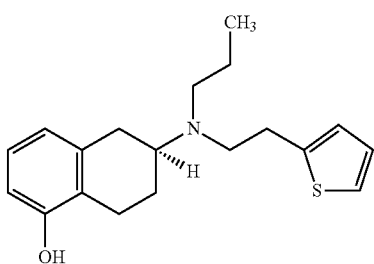 [SMILES: CCCN(CCc1cccs1)[C@H]1CCc2c(O)cccc2C1]

(15) Pardoprunox, represented by formula (33):

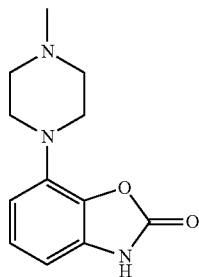 [SMILES: CN1CCN(c2cccc3[nH]c(=O)oc23)CC1]

preferably (8β)-8-[(methylthio)methyl]-6-propylergoline (pergolide; and herein also referred to as "compound B"), represented by formula (20):

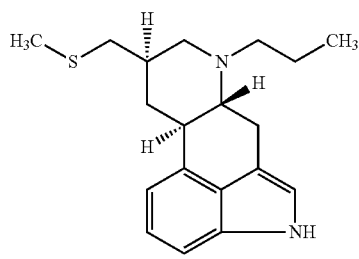 [SMILES: CCCN1C[C@H](CSC)C[C@@H]2c3cccc4[nH]cc(c34)C[C@H]21]

and/or (S)-2-Amino-6-(propylamino)-4,5,6,7-tetrahydrobenzothiazol (pramipexole), represented by formula (27):

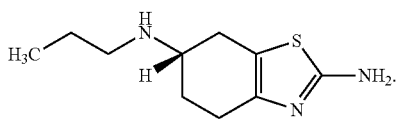

Metabolic Disorders

According to the invention, metabolic disorders or metabolic diseases are all kinds of disturbances of the energy metabolism, affecting e.g. the turnover of carbohydrates, proteins, and/or of fat. It is preferred to affect the control of the energy metabolism, especially the glucose metabolism by influencing the responsible regulatory network, e.g. via modulation of the activity and/or concentrations of insulin.

The metabolic disorder may be an insulin-related disorder. In particular, the metabolic disorder may be insulin resistance (or, equivalently, impaired insulin sensitivity). Insulin resistance may be associated with a further metabolic disorder or clinical condition, e.g. insulin resistance may be associated with impaired glucose tolerance, dyslipidaemia, dysadipokinaemia, subclinical inflammation, systemic inflammation, low grade systemic inflammation, chronic infections, muscle wasting, which also comprises adipose tissue, obesity and/or regional adiposity.

Additionally or alternatively, insulin resistance may be associated with laminitis. Additionally or alternatively, insulin resistance may be associated with vascular dysfunction. Additionally or alternatively, insulin resistance may be associated with hypertension. Additionally or alternatively, insulin resistance may be associated with hyperadrenocorticism. Additionally or alternatively, insulin resistance may be associated with hepatic lipidosis. Additionally or alternatively, insulin resistance may be associated with hirsutism. Additionally or alternatively, insulin resistance may be associated with hyperhidrosis. Additionally or alternatively, insulin resistance may be associated with polyuria. Additionally or alternatively, insulin resistance may be associated with polydipsia. Additionally or alternatively, insulin resistance may be associated with chronic infections. Additionally or alternatively, insulin resistance may be associated with abnormal fat distribution. Additionally or alternatively, insulin resistance may be associated with abnormal weight loss. Additionally or alternatively, insulin resistance may be associated with loss of appetite. Laminitis, vascular dysfunction, hypertension, hyperadrenocorticism, hepatic lipidosis, hirsutism, hyperhidrosis, polyuria, polydipsia, chronic infections, abnormal fat distribution, abnormal weight loss and/or loss of appetite are clinical conditions associated with EMS and/or PPID. Thus, additionally or alternatively, insulin resistance may be associated with EMS and/or PPID.

The metabolic disorder may be hyperinsulinaemia. Hyperinsulinaemia may be associated with a further metabolic disorder or clinical condition, e.g. hyperinsulinaemia may be associated with obesity and/or regional adiposity. Additionally or alternatively, hyperinsulinaemia may be associated with laminitis. Additionally or alternatively, hyperinsulinaemia may be associated with vascular dysfunction. Additionally or alternatively, hyperinsulinaemia may be associated with hypertension. Additionally or alternatively, hyperinsulinaemia may be associated with hepatic lipidosis. Laminitis, vascular dysfunction, hypertension, hyperadrenocorticism, hepatic lipidosis, hirsutism, hyperhidrosis, polyuria, polydipsia, chronic infections, abnormal fat distribution, abnormal weight loss and/or loss of appetite are clinical conditions associated with EMS and/or PPID. Thus or alternatively, hyperinsulinaemia may be associated with EMS and/or PPID.

In preferred embodiments, the metabolic disorder may be insulin resistance, hyperinsulinaemia and/or a clinical condition associated with insulin resistance and/or hyperinsulinaemia. Treatment or prevention of a metabolic disorder of an equine animal in accordance with the invention may be treatment or prevention of insulin resistance and/or hyperinsulinaemia.

Clinical conditions associated with insulin resistance and/or hyperinsulinaemia are e.g. impaired glucose tolerance, dyslipidaemia, dysadipokinaemia, subclinical inflammation, systemic inflammation, low grade systemic inflammation, which also comprises adipose tissue, obesity and/or regional adiposity. Treatment and/or prevention of a metabolic disorder of an equine animal in accordance with the invention may be the treatment and/or prevention of impaired glucose tolerance, dyslipidaemia, dysadipokinaemia, subclinical inflammation, systemic inflammation, low grade systemic inflammation, which also comprises adipose tissue, obesity and/or regional adiposity in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia may be impaired glucose tolerance. Hence, the treatment or prevention of a metabolic disorder of an equine animal in accordance with the invention may be the treatment or prevention of impaired glucose tolerance, preferably associated with insulin resistance and/or hyperinsulinaemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia may be dyslipidaemia. Hence, the treatment and/or prevention of a metabolic disorder of an equine animal in accordance with the invention may be the treatment and/or prevention of dyslipidaemia, preferably associated with insulin resistance and/or hyperinsulinaemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia may be dysadipokinaemia. Hence, the treatment and/or prevention of a metabolic disorder of an equine animal in accordance with the invention may be treatment and/or prevention of dysadipokinaemia, preferably associated with insulin resistance and/or hyperinsulinaemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia may be subclinical inflammation or systemic inflammation, in particular low grade systemic inflammation, which also comprises adipose tissue. Hence, the treatment and/or prevention of a metabolic disorder of an equine animal in accordance with the invention may be treatment and/or prevention of subclinical inflammation or systemic inflammation, in particular low grade systemic inflammation, which also comprises adipose tissue, preferably associated with insulin resistance and/or hyperinsulinaemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia may be obesity. Hence, the treatment and/or prevention of a metabolic disorder of an equine animal in accordance with the invention may be treatment and/or prevention of obesity, preferably associated with insulin resistance and/or hyperinsulinaemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia may be regional adiposity. Hence, the treatment and/or prevention of a metabolic disorder of an equine animal in accordance with the invention may be treatment and/or prevention of regional adiposity, preferably associated with insulin resistance and/or hyperinsulinaemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition, e.g. a metabolic disorder or clinical condition associated with insulin resistance and/or hyperinsulinaemia, may be laminitis. In some embodiments, laminitis may be associated with obesity and/or regional adiposity. In some embodiments, when a metabolic disorder or clinical condition is laminitis, the equine animal is suffering from EMS and/or PPID. The present invention preferably prevents the development and/or recurrence of laminitis, e.g., in an equine animal suffering from EMS and/or PPID.

Herein, a metabolic disorder or clinical condition, e.g. a metabolic disorder or clinical condition associated with insulin resistance and/or hyperinsulinaemia, may be vascular dysfunction, e.g. vascular dysfunction in an equine animal's hoof. In some embodiments, vascular dysfunction may be associated with obesity and/or regional adiposity. In some embodiments, when a metabolic disorder or clinical condition is vascular dysfunction, the equine animal is suffering from EMS and/or PPID. The present invention preferably prevents the development and/or recurrence of vascular dysfunction, e.g., in an equine animal suffering from EMS and/or PPID.

Herein, a metabolic disorder or clinical condition, e.g. a metabolic disorder or clinical condition associated with insulin resistance and/or hyperinsulinaemia, may be hypertension. In some embodiments, hypertension may be associated with regional obesity and/or regional adiposity. In some embodiments, when a metabolic disorder or clinical condition is hypertension, the equine animal is suffering from EMS and/or PPID. The present invention preferably prevents the development and/or recurrence of hypertension, e.g., in an equine animal suffering from EMS and/or PPID.

Herein, a metabolic disorder or clinical condition, e.g. a metabolic disorder or clinical condition associated with insulin resistance and/or hyperinsulinaemia, may be hepatic lipidosis. In some embodiments, hepatic lipidosis may be associated with regional obesity and/or regional adiposity. In some embodiments, when a metabolic disorder or clinical condition is hepatic lipidosis, the equine animal is suffering from EMS and/or PPID. The present invention preferably prevents the development and/or recurrence of hepatic lipidosis, e.g., in an equine animal suffering from EMS and/or PPID.

Herein, a metabolic disorder or clinical condition, e.g. a metabolic disorder or clinical condition associated with insulin resistance and/or hyperinsulinaemia, may be atherosclerosis, In some embodiments, atherosclerosis may be associated with systemic inflammation, subclinical inflammation, low grade systemic inflammation, which also comprises adipose tissue. In some embodiments, when a metabolic disorder or clinical condition is atherosclerosis, the equine animal is suffering from EMS and/or PPID. The present invention preferably prevents the development and/or recurrence of atherosclerosis, e.g., in an equine animal suffering from EMS and/or PPID.

Herein, a metabolic disorder or clinical condition, e.g. a metabolic disorder or clinical condition associated with insulin resistance and/or hyperinsulinaemia, may be hyperadrenocorticism. In some embodiments, hyperadrenocorticism may be associated with systemic inflammation, subclinical inflammation, low grade systemic inflammation, which also comprises adipose tissue. In some embodiments, when a metabolic disorder or clinical condition is hyperadrenocorticism, the equine animal is suffering from EMS and/or PPID. The present invention preferably provides for the treatment and/or prevention of hyperadrenocorticism, i.e. it prevents the development and/or recurrence of hyperadrenocorticism, e.g., in an equine animal suffering from EMS and/or PPID.

Herein, a metabolic disorder or clinical condition, e.g. a metabolic disorder or clinical condition associated with insulin resistance and/or hyperinsulinaemia, may be Equine Metabolic Syndrome (EMS). In some embodiments, EMS may be associated with obesity and/or regional adiposity.

Herein, a metabolic disorder or clinical condition, e.g. a metabolic disorder or clinical condition associated with insulin resistance and/or hyperinsulinaemia, may be Equine Pituitary Pars Intermedia Dysfunction (PPID). In some embodiments, PPID may be associated with hyperadrenocorticism.

In some embodiments, the equine animal treated in accordance with the invention (e.g. for hyperinsulinaemia, insulin resistance, and/or a clinical condition associated with insulin resistance and/or hyperinsulinaemia) is suffering from laminitis, vascular dysfunction, PPID and/or EMS.

In some embodiments, impaired glucose tolerance may be associated with obesity and/or regional adiposity. Hence, the treatment and/or prevention of a metabolic disorder of an equine animal in accordance with the invention may be treatment and/or prevention of impaired glucose tolerance associated with obesity and/or regional adiposity in an equine animal.

In some embodiments, impaired glucose tolerance may be associated with hyperadrenocorticism. Hence, the treatment and/or prevention of a metabolic disorder of an equine animal in accordance with the invention may be treatment and/or prevention of impaired glucose tolerance associated with hyperadrenocorticism in an equine animal.

In some embodiments, hyperadrenocorticism may be associated with hirsutism. Hence, the treatment and/or prevention of a metabolic disorder of an equine animal in accordance with the invention may be treatment and/or prevention of hyperadrenocorticism associated with hirsutism in an equine animal.

In some embodiments, hyperadrenocorticism may be associated with hyperhidrosis. Hence, the treatment and/or prevention of a metabolic disorder of an equine animal in accordance with the invention may be treatment and/or prevention of hyperadrenocorticism associated with hyperhidrosis in an equine animal.

In some embodiments, hyperadrenocorticism may be associated with polyuria. Hence, the treatment and/or prevention of a metabolic disorder of an equine animal in accordance with the invention may be treatment and/or prevention of hyperadrenocorticism associated with polyuria in an equine animal.

In some embodiments, hyperadrenocorticism may be associated with polydipsia. Hence, the treatment and/or prevention of a metabolic disorder of an equine animal in accordance with the invention may be treatment and/or prevention of hyperadrenocorticism associated with polydipsia in an equine animal.

In some embodiments, hyperadrenocorticism may be associated with abnormal fat distribution. Hence, the treatment and/or prevention of a metabolic disorder of an equine animal in accordance with the invention may be treatment and/or prevention of hyperadrenocorticism associated with abnormal fat distribution in an equine animal.

In some embodiments, hyperadrenocorticism may be associated with muscle wasting. Hence, the treatment and/or prevention of a metabolic disorder of an equine animal in accordance with the invention may be treatment and/or prevention of hyperadrenocorticism associated with muscle wasting in an equine animal.

In some embodiments, hyperadrenocorticism may be associated with abnormal weight loss. Hence, the treatment and/or prevention of a metabolic disorder of an equine animal in accordance with the invention may be treatment and/or prevention of hyperadrenocorticism associated with abnormal weight loss in an equine animal.

In some embodiments, hyperadrenocorticism may be associated with loss of appetite. Hence, the treatment and/or prevention of a metabolic disorder of an equine animal in accordance with the invention may be treatment and/or prevention of hyperadrenocorticism associated with loss of appetite in an equine animal.

In some embodiments, hyperadrenocorticism may be associated with chronic infections. Hence, the treatment and/or prevention of a metabolic disorder of an equine animal in accordance with the invention may be treatment and/or prevention of hyperadrenocorticism associated with chronic infections in an equine animal.

Insulin resistance can be described as the condition in which normal amounts of insulin are inadequate to produce a normal insulin response from fat, muscle and liver cells. Insulin resistance in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. Insulin resistance in muscle cells reduces glucose uptake (and so local storage of glucose as glycogen), whereas insulin resistance in liver cells results in impaired glycogen synthesis and a failure to suppress glucose production. Elevated blood fatty acid levels, reduced muscle glucose uptake, and increased liver glucose production, may all contribute to elevated blood glucose levels (hyperglycaemia), although hyperglycaemia is not a major issue e.g. in insulin-resistant horses. In the horse, when insulin-resistant target tissues, e.g. skeletal muscle, have a reduced capacity for glucose uptake, the pancreas is stimulated to release more insulin, leading to hyperinsulinaemia.

Surrogate indices of insulin sensitivity may be calculated according to the QUICKI (quantitative insulin sensitivity check index: $1/\log(\text{glucose}*\text{insulin})$) for basal blood level. For dynamic testings, e.g. during a glucose challenge a modified Belfiore Index ($1/\log(\Delta\text{AUC-glucose}*\Delta\text{AUC-insulin})$) can be employed.

Insulin resistance may be present in association with regional adiposity, e.g. cresty neck, tail fat depots, visceral adiposity, hypertension and dyslipidaemia involving elevated triglycerides, small dense low-density lipoprotein (sdLDL) particles, and decreased HDL cholesterol levels. With respect to visceral adiposity, a great deal of evidence in humans suggests two strong links with insulin resistance. First, unlike subcutaneous adipose tissue, visceral adipose cells produce significant amounts of pro-inflammatory cytokines such as tumor necrosis factor-alpha (TNF-α), and Interleukins-1 and -6, etc. In numerous experimental models, these pro-inflammatory cytokines profoundly disrupt normal insulin action in fat and muscle cells, and may be a major factor in causing the whole-body insulin resistance observed in human patients with visceral adiposity. Similar, in equines the different excessive regional fat depots contribute to low grade systemic inflammation. Second, adiposity is related to an accumulation of fat in the liver, a condition known as non-alcoholic fatty liver disease (NAFLD) in humans and hepatic lipidosis in general terms, e.g. in equines. The result of NAFLD is an excessive release of free fatty acids into the bloodstream (due to increased lipolysis), and an increase in hepatic glucose production, both of which have the effect of exacerbating peripheral insulin resistance. The cause of the vast majority of cases of insulin resistance remains unknown. There is clearly an inherited component. However, there are some grounds for suspecting that insulin resistance is related to a high-carbohydrate diet. Inflammation also seems to be implicated in causing insulin resistance.

Hyperinsulinaemia can be described as a condition in which there are excess levels, i.e. more than about 10-20 µIU/mL of insulin circulating in the blood. As mentioned, it is commonly present in cases of, and may be a consequence of, insulin resistance in equine animals.

Impaired glucose tolerance can be described as condition in which the response to a glycaemic challenge e.g. after a meal or after a loading test (glucose tolerance test) the glycaemic peak of the glucose excursion is higher and/or the duration of the glucose excursion is prolonged.

Dyslipidaemia or hyperlipidaemia is the presence of raised or abnormal levels of lipids and/or lipoproteins in the blood. Lipid and lipoprotein abnormalities are regarded as a highly modifiable risk factor for cardiovascular disease due to the influence of cholesterol, one of the most clinically relevant lipid substances, on atherosclerosis. Glycerol is a precursor for the synthesis of triacylglycerols (triglycerides) and of phospholipids in the liver and adipose tissue. When the body uses stored fat as a source of energy, glycerol and fatty acids are released into the bloodstream after hydrolysis of the triglycerides. The glycerol component can be converted to glucose by the liver and provides energy for cellular metabolism. Normal levels of free fatty acids in the blood equine animals are concentrations of 50 to 100 mg/dl (0.6 to 1.2 mmol/l). Normal levels of triglycerides are e.g. up to around 50 mg/dl. Normal levels of blood cholesterol are, e.g., around 120 mg/dl for the horse.

Dysadipokinaemia can be described as a condition in which the circulating plasma levels of biologically active substances produced in adipose tissue that act in an autocrine/paracrine or endocrine fashion is deviated, e.g. an elevation of leptin and/or a reduction of adiponectin.

Subclinical inflammation or systemic inflammation, in particular low grade systemic inflammation is characterized by increased expression and secretion of pro-inflammatory cytokines such as tumor necrosis factor-alpha and/or lower expression and secretion of anti-inflammatory cytokines e.g. interleukin-10 and/or their respective receptors.

Laminitis can be described as an inflammation or edema of the sensitive laminae of the hoof resulting e.g. in lameness. The laminae bond the hoof wall to the pedal bone, which supports the entire weight of the horse or equine. Severe cases of laminitis can result in the pedal bone rotation that may progress to perforation of the sole. Laminitis-induced lameness can be graded e.g. by visual score of behavior in standing position and moving performance.

Vascular dysfunction can be described as impaired action of endothelium-dependent insulin induced vasodilation, as well alteration of direct insulin effects on vascular smooth muscles, e.g. relaxation and reactivity to vasoconstrictor stimuli.

Equine Metabolic Syndrome (EMS) is defined by the presence of insulin resistance, obesity and/or regional adiposity. The EMS phenotype may also comprise dyslipidaemia, dysadipokinaemia and/or hypertension. The syndrome can be described as a combination of medical disorders that increase the risk of developing associated pathologies, e.g. laminitis. The equine metabolic syndrome might also be associated with other disorders like hepatic lipidosis or infertility.

Obesity can be described as a medical condition in which excess body fat has accumulated to the extent that it may have an adverse effect on health, leading to reduced life expectancy. In equines e.g. during physical examination a body condition scores of equal or more than 7 (out of 9) is encountered.

Regional adiposity in equine animals can be described as a medical condition in which body fat (adipose tissue) accumulates in specific regions, e.g. the neck (cresty neck), either side of the tailhead, prepuce, in fat pads in the rump area, the mammary gland region, and/or in supraorbital fat pads. Regional adiposity also encompasses visceral adiposity, e.g. increased omental fat.

Obesity and or regional adiposity is associated with many other diseases, particularly heart disease, type 2 diabetes (though this is rare in horses), certain types of cancer, osteoarthritis and/or strangulating lipoma. Obesity is most commonly caused by a combination of excessive dietary calories, lack of physical activity, and genetic susceptibility, though a limited number of cases are due to a single cause, e.g. solely to genetics.

Atherosclerosis can be described as a condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

Pituitary Pars Intermedia Dysfunction (PPID) is a common disease of older horses and ponies. Hypothalamic dopaminergic neurodegeneration results in an elevated adrenocorticotropic hormone (ACTH) production in the Pituitary Pars Intermedia and leads to hyperadrenocorticism. Clinical signs include hirsutism (a long, often curly coat that may not shed), polydipsiapolyuria, excessive sweating, weight loss, muscle wasting, regional fat deposits, lethargy, infections (e.g. sinusitis) and/or laminitis.

Hirsutism is a long, non-shedding hair coat. The long hair growth can be restricted to discrete areas, e.g. the lower jaw, base of the neck, and palmar/plantar parts of the distal limbs. The long hair growth can also occur over the entire body. In addition, the hair can also be curly. Typically, the hair coat fails to shed out.

Hyperhidrosis is an abnormal sweating. This can include regional sweating or generalized sweating over the entire body.

Polyuria is a condition defined as excessive or abnormally large production or passage of urine. Polyuria often appears in conjunction with polydipsia, though it is possible to have one without the other, and the latter may be a cause or an effect. Polyuria is physiologically normal in some circumstances, such as diuresis and after drinking large amounts of fluids. The most common cause of polyuria is uncontrolled diabetes mellitus causing an osmotic diuresis. In the absence of diabetes mellitus, polyuria can also be caused by diabetes insipidus (central diabetes insipidus or renal diabetes insipidus).

Polydipsia is a condition defined as excessive thirst. Polydipsia often appears in conjunction with polyuria, though it is possible to have one without the other.

Abnormal fat distribution is a condition where the body fat is abnormally distributed within the body. This can be combined with regional adiposity.

Muscle wasting is a condition of a gradual decrease in the mass of the muscle.

Abnormal weight loss is a condition of losing body weight without an obvious cause for the loss of body weight.

Loss of appetite is a condition of less appetite than normal.

Equine Animals

Herein, the term "equine animal" may be used interchangeably with the term "equine" and encompasses any member of the genus *Equus*. It encompasses, e.g., any horse or pony, the taxonomic designations *Equus ferus* and/or *Equus caballus*, and/or the subspecies *Equus ferus caballus*. The equine animal may, e.g., be a domestic horse.

Pharmaceutical Compositions and Formulations

SGLT2 inhibitors and dopamine receptor agonists for the combined use according to the invention may be prepared as pharmaceutical compositions. They may be prepared as solid or as liquid formulations. In either case, they are preferably prepared for oral administration. The SGLT2 inhibitors and dopamine receptor agonists may, however, also be prepared, e.g., for parenteral administration.

A unit for administration, e.g. a single liquid dose or a unit of a solid formulation, e.g. a tablet, may comprise 5 mg to 2500 mg, or e.g. 5 mg to 2000 mg, 5 mg to 1500 mg, 10 mg to 1500 mg, 10 mg to 1000 mg, or 10 mg to 500 mg of one or more SGLT2 inhibitors and 5 mg to 1500 mg, or e.g. 10 mg to 500 mg, or e.g. 15 mg to 200 mg of one or more dopamine receptor agonists for use according to the invention. As the skilled person would understand, the content of the one or more SGLT2 inhibitors and one or more dopamine receptor agonists in a solid formulation, or any formulation as disclosed herein for administration to an equine animal, may be increased or decreased as appropriate in proportion to the body weight of the equine animal to be treated.

In one embodiment a pharmaceutical composition for use according to the invention is designed for oral or parenteral administration, preferably for oral administration. Especially the oral administration is ameliorated by excipients which modify the smell and/or haptic properties of the pharmaceutical composition for the intended patient, e.g. as described.

When the one or more SGLT2 inhibitors and one or more dopamine receptor agonists for the combined use according to the invention is formulated for oral administration, it is preferred that excipients confer properties, e.g. palatability and/or chewability that render the formulation suitable for administration to an equine animal.

Dosing and Administration

A practitioner skilled in the art can determine suitable doses for the uses of the present invention. Preferred units dosing units include mg/kg, i.e. mg SGLT2 inhibitor per body mass of the equine animal. An SGLT2 inhibitor of the invention may, e.g., be administered in doses of 0.01-5 mg/kg bodyweight per day, e.g. 0.01-4 mg/kg, e.g. 0.01-3 mg/kg, e.g. 0.01-2 mg/kg, e.g. 0.01-1.5 mg/kg, e.g., 0.01-1 mg/kg, e.g. 0.01-0.75 mg/kg, e.g. 0.01-0.5 mg/kg, e.g. 0.01-0.4 mg/kg, e.g. 0.01-0.4 mg/kg bodyweight per day. Preferably the dose is 0.02-0.5 mg/kg bodyweight per day, more preferably 0.03-0.4 mg/kg bodyweight per day, e.g. 0.03-0.3 mg/kg bodyweight per day.

In a preferred embodiment, the one or more SGLT2 inhibitors or pharmaceutically acceptable forms and/or salts thereof may be administered in dosages of 0.01 to 3.0 mg/kg body weight per day, preferably from 0.02 to 1.0 mg/kg bodyweight per day, more preferably from 0.03 to 0.4 mg/kg bodyweight per day. Thus, the one or more SGLT2 inhibitors or pharmaceutically acceptable forms and/or salts thereof may be prepared for the administration of 0.01 to 3.0 mg/kg bodyweight per day, preferably from 0.02 to 1.0 mg/kg bodyweight per day, more preferably from 0.03 to 0.4 mg/kg bodyweight per day.

A practitioner skilled in the art is able to prepare an SGLT2 inhibitor of the invention for administration according to a desired dose.

Preferably, according to the invention, an SGLT2 inhibitor is administered no more than three times per day, more preferably no more than twice per day, most preferably only once per day. The frequency of administration can be adapted to the typical feeding rate of the equine animal.

Preferably, following administration and the time required for the SGLT2 inhibitor to reach the bloodstream, such levels are maintained in the blood over a time interval of at least 12 hours, more preferably at least 18 hours, most preferably at least 24 h.

Preferably, according to the invention, an SGLT2 inhibitor is administered orally, in liquid or solid form. The SGLT2 inhibitors may, however, also be administered, e.g., parenterally, or by any other route of administration, e.g., rectally.

Preferred units dosing units include µg/kg, i.e. µg dopamine receptor agonist per body mass of the equine animal. A dopamine receptor agonist of the invention may, e.g., be administered in doses of 0.01 to 100 µg/kg bodyweight per day, e.g. 0.1 to 100 µg/kg bodyweight per day, e.g. 0.1 to 10 µg/kg bodyweight per day, e.g. 0.06 to 10 µg/kg bodyweight per day, e.g. 2.0 µg/kg bodyweight per day.

In a preferred embodiment, the one or more dopamine receptor agonist or pharmaceutically acceptable forms and/or salts thereof may be administered in dosages of from 0.01 to 100 µg/kg bodyweight per day, preferably from 0.1 to 100 µg/kg bodyweight per day, more preferably from 0.1 to 10 gig/kg bodyweight per day. Thus, the one or more dopamine receptor agonist or pharmaceutically acceptable forms and/or salts thereof may be prepared for the administration of from 0.01 to 100 µg/kg bodyweight per day, preferably from 0.1 to 100 µg/kg bodyweight per day, more preferably from 0.1 to 10 µg/kg bodyweight per day.

A practitioner skilled in the art is able to prepare a dopamine receptor agonist of the invention for administration according to a desired dose.

Preferably, according to the invention, a dopamine receptor agonist is administered no more than three times per day, more preferably no more than twice per day, most preferably only once per day. The frequency of administration can be adapted to the typical feeding rate of the equine animal.

Preferably, following administration and the time required for the dopamine receptor agonist to reach the bloodstream, such levels are maintained in the blood over a time interval of at least 12 hours, more preferably at least 18 hours, most preferably at least 24 h.

Preferably, according to the invention, a dopamine receptor agonist is administered orally, in liquid or solid form. The dopamine receptor agonists may, however, also be administered, e.g., parenterally, or by any other route of administration, e.g., rectally.

EXAMPLES

The following examples serve to further illustrate the present invention; but the same should not be construed as a limitation of the scope of the invention disclosed herein.

Example 1 The Effect of a Combination of One SGLT2 Inhibitor (Compound A) and One Dopamine Receptor Agonist (Compound B) on Postprandial Blood Glucose in Horses The acute effect of a combination treatment with Compound A and Compound B on postprandial blood glucose in horses can be studied e.g. in overnight fasted horses. E.g. two hours after compound administration horses are fed a test meal and the postprandial glycaemia is quantified 2 hours thereafter. Values can be compared with the values before the start of the study and/or with those of a placebo group and/or the respective monotherapies with the one SGLT2 inhibitor and the one dopamine receptor agonist.

The efficacy of combination of SGLT2 inhibition and dopamine receptor agonism in accordance with the invention in the treatment of pathological fasting glucose and/or insulin and/or impaired glucose tolerance can be tested using clinical studies. In studies over a shorter or longer period (e.g. 2-4 weeks or 1-2 years) the success of the treatment is examined by determining the fasting glucose and insulin values and/or the glucose values after a meal or after a loading test (oral glucose tolerance test or food tolerance test after a defined meal) after the end of the period of therapy for the study. Values can be compared with the values before the start of the study and/or with those of a placebo group and/or the respective monotherapies with the one SGLT2 inhibitor or the one dopamine receptor agonist. In addition, the fructosamine value can be determined before and after therapy and compared with the initial value and/or the placebo value and/or the respective monotherapies with the one SGLT2 inhibitor or the one dopamine receptor agonist. A significant drop in the fasting or non-fasting glucose and/or insulin and/or fructosamine levels demonstrates the efficacy of the treatment.

Example 2 Effects of a Combination of One SGLT2 Inhibitor (Compound A) and One Dopamine Receptor Agonist (Compound B) on Equine Pituitary Pars Intermedia Dysfunction (PPID) and Associated Diseases Such as Insulin Resistance and/or Laminitis Combination treatment with Compound A and Compound B can be studied in horses with metabolic disorders according to the present invention. Particularly in studies in horses with Equine Pituitary Pars Intermedia Dysfunction (PPID) and associated diseases such as laminitis running for different lengths of time (e.g. 2 weeks to 12 months or 2 to 3 years) e.g. the success of the improvement in insulin resistance can be checked using the measurement of baseline blood glucose, blood fructosamine and blood insulin level and their corresponding relation (surrogate indices) in the individual horse. Also the glucose and insulin values after a meal or after a loading test (glucose tolerance test or insulin tolerance test) after or during a period of therapy can be analyzed. Values can be compared with the values before the start of the study and/or with those of a placebo group and/or the respective monotherapies with Compound A or Compound B. Additionally, the incidence of laminitis and/or the reduction of lameness and/or time to recovery from a laminitis episode can be evaluated with respect to the initial lameness values and the time course of lameness throughout an observation period.

Also the comparison with a placebo group or a group given a different therapy can prove the efficacy of a pharmaceutical composition according to the invention.

Example 3 The Effect of a Combination of One SGLT2 Inhibitor (Compound A) and One Dopamine Receptor Agonist (Compound B) on Blood ACTH Level in Horses The acute effect of a combination treatment with Compound A and Compound B on blood ACTH level in horses can be studied e.g. measuring basal blood samples of overnight fasted horses. Alternatively stimulation tests as described earlier can be employed.

Values can be compared with the values before the start of the study and/or with those of a placebo group and/or the respective monotherapies with Compound A or Compound B.

Particularly in studies in horses with Equine Pituitary Pars Intermedia Dysfunction (PPID) exhibiting elevated blood ACTH concentration running for different lengths of time (e.g. 2 weeks to 12 months or 2 to 3 years) e.g. the success of the improvement in insulin resistance can be assessed as described above.

Additionally, the effects of the combination treatment with Compound A and Compound B on blood ACTH level in horses can be studied e.g. measuring basal blood samples of overnight fasted horses. Alternatively stimulation tests as described earlier can be employed.

Values can be compared with the values before the start of the study and/or with those of a placebo group and/or the respective monotherapies with Compound A or Compound B.

REFERENCES (1) EP 0 003 667
(2) EP 0 026 671
(3) EP 0 213 850
(4) EP 1 213 296
(5) EP 1 354 888
(6) EP 1 344 780
(7) EP 1 489 089
(8) Frank N et al., "Diagnosis and Treatment of Pituitary Pars Intermedia Dysfunction (PPID)", The PPID Working Group, September 2011
(9) Gehlen, 2014 Journal of Equine Veterinary Science 34(4): 508-513
(10) Katz & Bailey, 2012 Equine Veterinary Journal 44:752-761
(11) McGowan, 2004 Equine vet. J. 36 (3) 295-298
(12) McGowan, 2005 The Veterinarian, Clinical Review 26/1/05
(13) Tinworth et al., 2012 The Veterinary Journal 191:79-84
(14) Treiber et al., 2006 The Journal of Nutrition 136 (7 Suppl):2094S-2098S
(15) U.S. Pat. No. 3,732,231
(16) U.S. Pat. No. 3,901,894
(17) U.S. Pat. No. 3,920,664
(18) U.S. Pat. No. 3,959,288
(19) U.S. Pat. No. 4,166,182
(20) U.S. Pat. No. 4,246,265
(21) U.S. Pat. No. 4,782,152
(22) Venugopal et al., 2011 Equine Veterinary Journal 43:744-749
(23) WO 96/40139
(24) WO01/27128

(25) WO 02/11727
(26) WO 03/099836
(27) WO 2004/007517
(28) WO 2004/080990
(29) WO 2005/012326
(30) WO 2005/092877
(31) WO 2006/034489
(32) WO 2006/064033
(33) WO 2006/117359
(34) WO 2006/117360
(35) WO 2006/120208
(36) WO 2007/025943
(37) WO 2007/028814
(38) WO 2007/031548
(39) WO 2007/093610
(40) WO 2007/114475
(41) WO 2007/128749
(42) WO 2007/129053
(43) WO 2007/140191
(44) WO 2008/002824
(45) WO 2008/013280
(46) WO 2008/042688
(47) WO 2008/049923
(48) WO 2008/055870
(49) WO 2008/055940
(50) WO 2008/069327
(51) WO 2008/116179
(52) WO 2009/014970
(53) WO 2009/022020
(54) WO 2009/022008
(55) WO 2009/035969
(56) WO 2010/023594
(57) WO 2011/039108
(58) WO 2011/039107
(59) WO2014/016381

The invention claimed is:

1. A method for treating a metabolic disorder in an equine in need of such treatment comprising administering to the equine an effective amount of a medicament comprising one or more SGLT2 inhibitors, pharmaceutically acceptable forms or salts thereof in combination with one or more dopamine receptor agonists, pharmaceutically acceptable forms or salts thereof, wherein:
the one or more SGLT2 inhibitors comprises 1-cyano-2-(4-cyclopropyl-benzyl)-4-(β-D-glucopyranos-1-yl)-benzene, represented by the formula:

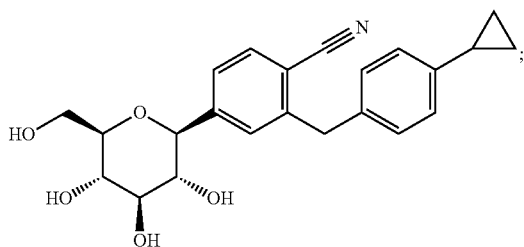 [SMILES: N#Cc1ccc([C@@H]2O[C@H](CO)[C@@H](O)[C@H](O)[C@H]2O)cc1Cc1ccc(C2CC2)cc1]

and
the one or more dopamine receptor agonists comprises (8β)-8-[(methylthio)methyl]-6-propylergoline (pergolide), represented by the formula:

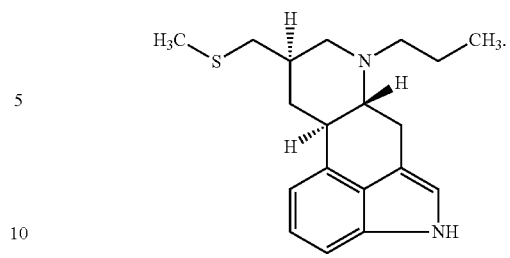

2. The method according to claim 1, wherein said metabolic disorder is one or more disorders selected from the group consisting of: Equine Metabolic Syndrome (EMS), Equine Pituitary Pars Intermedia Dysfunction (PPID), laminitis, vascular dysfunction, hypertension, hepatic lipidosis, hyperadrenocorticism, glucose intolerance, insulin resistance, hyperinsulinaemia, hirsutism, hyperhidrosis, polyuria, polydipsia, abnormal fat distribution, muscle wasting, abnormal weight loss, loss of appetite and combinations thereof.

3. The method according to claim 2, wherein the treatment of a metabolic disorder of an equine animal is treatment of clinical symptoms associated with Equine Pituitary Pars Intermedia Dysfunction (PPID), wherein such clinical symptoms are selected from the group consisting of: laminitis, vascular dysfunction, hypertension, hepatic lipidosis, hyperglycaemia, glucose intolerance, insulin resistance, hyperinsulinaemia, hirsutism, hyperhidrosis, polyuria, polydipsia, abnormal fat distribution, muscle wasting, abnormal weight loss, loss of appetite and combinations thereof.

4. The method according to claim 1, wherein the combination is administered through simultaneous administration, sequential (in any order) administration, or chronologically staggered administration.

5. The method according to claim 1, wherein the equine animal is a horse or a pony.

6. The method according to claim 1, wherein the medicament is administered orally or parenterally.

7. The method according to claim 1, wherein the one or more SGLT2 inhibitors, pharmaceutically acceptable forms, or salts thereof are administered at a dose of 0.01 to 5 mg/kg bodyweight per day.

8. The method according to claim 7, wherein the one or more dopamine receptor agonists, pharmaceutically acceptable forms, or salts thereof are administered at a dose of 0.01 to 100 µg/kg bodyweight per day.

9. The method according to claim 1, wherein the one or more SGLT2 inhibitors, pharmaceutically acceptable forms, or salts thereof are administered only once per day.

10. The method according to claim 1, wherein the one or more dopamine receptor agonists, pharmaceutically acceptable forms, or salts thereof are administered only once per day.

11. The method according to claim 1, wherein the one or more SGLT2 inhibitors, pharmaceutically acceptable forms, or salts thereof are administered at a dose of 0.02 to 1.0 mg/kg bodyweight per day.

12. The method according to claim 11, wherein the one or more dopamine receptor agonists, pharmaceutically acceptable forms, or salts thereof are administered at a dose of 0.1 to 100 µg/kg bodyweight per day.

13. The method according to claim 11, wherein the one or more dopamine receptor agonists, pharmaceutically acceptable forms, or salts thereof are administered at a dose of 0.1 to 10 µg/kg bodyweight per day.

14. The method according to claim 1, wherein the one or more SGLT2 inhibitors, pharmaceutically acceptable forms, or salts thereof are administered at a dose of 0.03 to 0.4 mg/kg bodyweight per day.

15. The method of claim 1, wherein the one or more SGLT2 inhibitors further includes a crystalline complex between the 1-cyano-2-(4-cyclopropyl-benzyl)-4-(β-D-glucopyranos-1-yl)-benzene and one or more amino acids.

16. The method of claim 15, wherein the one or more amino acids comprises proline.

17. The method of claim 16, wherein the one or more amino acids comprises L-proline.

18. A method for treating a metabolic disorder in an equine in need of such treatment comprising administering to the equine in combination an effective amount of an SGLT2 inhibitor or a pharmaceutically acceptable form or salt thereof with an effective amount of a dopamine receptor agonist or a pharmaceutically acceptable form or salt thereof, wherein:
the SGLT2 inhibitor consists of 1-cyano-2-(4-cyclopropyl-benzyl)-4-(β-D-glucopyranos-1-yl)-benzene represented by formula:

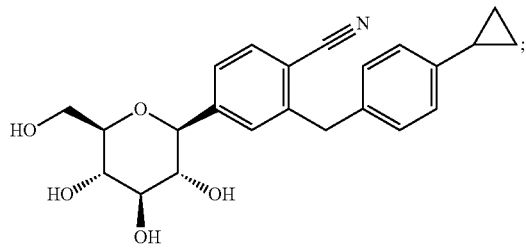 [SMILES: N#Cc1ccc([C@@H]2O[C@H](CO)[C@@H](O)[C@H](O)[C@H]2O)cc1Cc1ccc(C2CC2)cc1]

and the dopamine receptor agonist consists of (8β)-8-[(methylthio)methyl]-6-propylergoline (pergolide) represented by the formula:

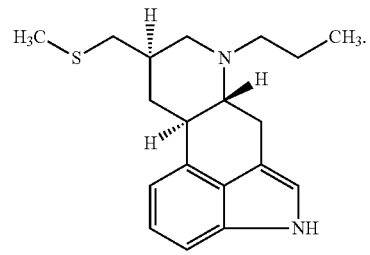 [SMILES: CCCN1C[C@H](CSC)C[C@@H]2c3cccc4[nH]cc(c34)C[C@H]21]

* * * * *